United States Patent [19]

Chan et al.

[11] Patent Number: 4,831,185

[45] Date of Patent: May 16, 1989

[54] ASYMMETRIC SYNTHESIS OF NATURAL VITAMIN E

[75] Inventors: Ka-kong Chan, Hopatcong, N.J.; Gabriel G. Saucy, Vero Beach, Fla.

[73] Assignee: Hoffmann-La Roche Inc., Nutley, N.J.

[21] Appl. No.: 135,128

[22] Filed: Dec. 18, 1987

[51] Int. Cl.[4] .............................................. C07C 69/76
[52] U.S. Cl. ...................................... 560/85; 560/106; 560/109
[58] Field of Search .......................... 560/85, 106, 109

[56] References Cited

U.S. PATENT DOCUMENTS 4,626,276 12/1986 Luo ..................................... 560/106

FOREIGN PATENT DOCUMENTS 1231005 4/1985 Japan ..................................... 560/85

OTHER PUBLICATIONS

Mayer, et al., Helv. Chimica Acta vol. 67, pp. 650-671 (1983.

*Primary Examiner*—Asok Pal
*Attorney, Agent, or Firm*—Jon S. Saxe; George M. Gould; William H. Epstein

[57] ABSTRACT

An asymmetric synthesis for Vitamin E in an optically active pure form for 4-(2,5-diloweralkanoyloxy)-3,4,6-trimethylphenyl-butan-2-one and intermediates therein.

17 Claims, No Drawings

ASYMMETRIC SYNTHESIS OF NATURAL VITAMIN E

BACKGROUND OF INVENTION

The publication of Mayer et al. in Helv. Chimca. Acta, Volume 67, pgs. 650-671 (1963) discloses the preparation of Vitamin E which has the formula:

[Structure I]

from a compound of the formula:

[Structure II]

by first coupling the compound of formula II by means of a Grignard reagent with acetylene to form a compound of the formula:

[Structure III]

The compound of III was then cyclized by treating with an inorganic acid such as sulfuric acid in an inert organic solvent such as dioxane to form a racemic compound of formula:

[Structure IV]

The compound of formula IV was then converted to optically active Vitamin E through several intermediates. However in order to produce optically active Vitamin E, Meyer, et al found it necessary to resolve these intermediates using optically active amines, with consequent loss of yield.

SUMMARY OF INVENTION

The invention, provides a new process for producing optically active natural Vitamin E which has the structure:

[Structure I-A]

from the compound of formula:

[Structure III-A]

where R taken together with its attached oxygen atom forms a hydrolyzable ester hydroxy protecting group.

This asymmetric synthesis is accomplished by the spontaneous resolution through crystallization of either a racemic compound of the formula:

[Structure V]

where R is as above and $R_4$ is phenyl or phenyl substituted with from 1 to 3 halo groups into its optically active enantiomers

[Structure V-A]

and

[Structure V-B]

wherein R and $R_4$ are as above or a compound of the formula

[Structure VI]

into its optically active enantiomers of the formula

[Structure VI-A]

and

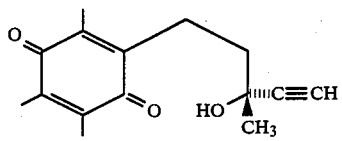

VI-B

The compounds of formula V-A and VI-A have the correct stereoconfiguration for natural optically active Vitamin E and can be converted to natural optically active Vitamin E. In accordance with this invention, the compounds of formula V-B and VI-B which are the unwanted stereoisomers can be converted back to the isomers having the desired stereoconfiguration for natural Vitamin E. Therefore through the synthesis of this invention, natural vitamin E having the optically active configuration of formula I-A can be stereospecifically produced from the compound of formula III-A without loss of yield through resolution. In producing the compounds of formula I-A, in accordance with this invention, one starts from a compound of the formula

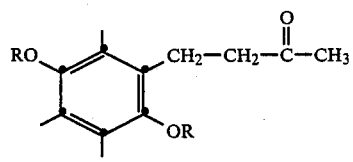

II-A wherein R is as above.

DETAILED DESCRIPTION

As used throughout this application, the term "lower alkyl" includes both straight chain and branched chain alkyl groups having from 1 to 7 carbon atoms such as methyl and ethyl. As used herein, the term "lower alkoxy" denotes lower alkoxy groups containing 1 to 7 carbon atoms preferably 1 to 7 carbon atoms, such as methoxy, ethoxy, i-propoxy, t-butoxy, etc. As also used herein, the term "lower alkanoic acid" comprehends an alkanoic acid of from 1 to 7 carbon atoms such as formic acid and acetic acid. The term "lower alkanyl" designates the monovalent radical formed from a lower alkanoic acid by removal of the OH group on the COOH moiety. Among the preferred lower alkanoyl groups are acetyl, pivaloyl, butyryl, propionyl with acetyl being especially preferred. As further used herein, the term "halogen" or "halo", unless otherwise stated, comprehends all halogens such as fluorine, chlorine, bromine and iodine. Alkali metal includes all alkali metals such as lithium, sodium and potassium.

In the pictorial representation of the compounds given throughout this application, a thickened taper line (⎯⎯) indicates a substituent which is in the beta-orientation (above the plane of the molecule), a broken line (≡) indicates a substituent which is in the alpha-orientation (below the plane of the molecule) and a wavy line ( ∫ ) indicates a substituent which is in either the alpha- or beta-orientation or mixtures of these isomers.

As also used herein, the term "aryl" signifies mononuclear aromatic hydrocarbon groups such as phenyl, which can be unsubstituted or substituted in one or more positions with a lower akylenedioxy, nitro, halo, a lower alkyl or a lower alkoxy substitutent, and polynuclear aryl groups such as naphthyl, anthryl, phenanthryl, etc., which can be unsubstituted or substituted with one or more of the aforementioned groups. The preferred aryl groups are the substituted and unsubstituted mononuclear aryl groups, particularly phenyl.

The term "ether hydroxy protecting group" designates any ether group for protecting a hydroxy group which, upon acid catalyzed cleavage or hydrogenolysis yields the free hydroxy group. Suitable ether protecting groups are, for example, the tetrahydropyranyl, benzyl, t-butyl or 4-tetrahydropyranyl ethers. Others are arylmethyl ethers such as benzhydryl, or trityl ethers or alpha-lower alkoxy-lower alkyl ether, for example, methoxymethyl or tri(lower alkyl)silyl ethers such as trimethylsilyl ether, diethyl-t-butylsilyl ether or dimethyl-tert-butylsilyl ether. Acid catalyzed cleavage is carried out by treatment with an organic or inorganic acid. Among the preferred inorganic acids are the mineral acids such as sulfuric acid, hydrohalic acid, etc. Among the preferred organic acids are lower alkanoic acids such as acetic acid, para-toluenesulfonic acid, etc. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out such cleavage, temperature and pressure are not critical and this reaction can be carried out at room temperature and atmospheric pressure.

The term "hydrolyzable ester hydroxy protecting group" denotes ester protecting groups where the hydroxy substitutent is protected by esterification with an organic acid to form an ester which upon hydrolysis yields the free hydroxy substitutent. Among the preferred hydrolyzable esters which can be utilized to protect the hydroxy group are those esters formed by reacting the hydroxy group with a lower alkanoic acid containing from 1 to 7 carbon atoms present as acetic acid, propionic acid, butyric acid, as well as aroic acids such as benzoic acid and carbonic acids of the formula

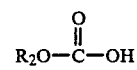

wherein $R_2$ is lower alkyl or aryl as well as lower alkoxy-lower alkanoic acids where lower alkoxy is as above and the lower alkanoic acids contain from 2 to 7 carbon atoms.

In accordance with this invention, the compound of formula II-A is converted to the compound of formula III-A by coupling with acetylene. Any conventional method of coupling a ketone with acetylene can be utilized to carry out this conversion. Among the preferred methods is by reacting the compound of formula II-A with an alklai metal acetylide. On the other hand the compound of formula II-A can be reacted directly with acetylene gas in the presence of a catalyst such as lithium metal. Any of the conditions conventionally utilized in carrying out these reactions can be utilized. However, temperatures of from −70° C. to −30° C. should be utilized to prevent the hydrolysis of the ester groups.

The compound of formula III-A is converted to the formula V by esterification with benzoic acid or a halo substituted benzoic acid or reactive derivatives thereof. Any conventional method of esterification can be utilized to convert the compound of formula III-A to the compound of formula V. In forming the ester of formula V, the preferred reactive derivatives are the acid halides or the acid anhydrides. In the compound of formula V, $R_4$ can be any halo-substituted phenyl moiety such as m-chloro, o-bromo and p-bromo. On the other hand, the phenyl group can be substituted with different halo groups. Among the preferred phenyl groups are 2,3-dichorophenyl, 2-chloro-3-bromo-phenyl or 3-iodo-2-chloro-phenyl.

The compound of formula V can be separated into its two diastereomers i.e. the compound of formula V-A and the compound of formula V-B. This separation occurs by dissolving the compound of formula V in a hydrocarbon solvent preferable an aromatic hydrocarbon solvent such as benzene, toluene or xylene. In accordance with this invention it has been found that when the compound of formula V is dissolved in an aromatic hydrocarbon solvent, a solution results from which the two stereoisomers of the compound of formula V can be easily separated. Any conventional method of separation can be used for obtaining the stereoisomers. One method is by seeding the solution with the desired isomer so that this desired isomer can be recovered in crystalline form from the solution. Therefore, by seeding with crystals of the compound of formula V-A, one obtains the compound of formula V-A, in crystalline form from the solution leaving the compound of formula V-B in solution. In carrying out this spontaneous crystallization, temperature and pressure are not critical and this procedure can be carried out at room temperature. Normally it is preferred to carry out this reaction at any temperature of from +20° C. to +40° C.

To prepare the desired isomer in crystalline form needed for seeding the desired isomer of formula V from the solution containing the compound of formula V, the compound of formula V can be resolved into its optically active antipodes by utilizing any conventional method for resolving alcohol. The preferred method is to react the compound of formula III-A with a dicarboxylic acid particularly an acid of the formula

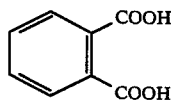      X

In forming the ester, the compound of formula III-A is reacted with a reactive derivative of the compound of formula X such as an anhydride. The ester formed thereby will have a free carboxy group which can be reacted with an optically active amine conventionally used for resolution. Among the preferred optically active amines are included alpha-methylbenzylamine or dehydroabietlyamine. Any other conventional optically active amine can be utilized in converting the compound of formula V into its optical active amines salts. The diastereomeric mixture formed by the reaction of the free carboxylic acid group on the ester with an optically active amine can be separated by conventional methods such as crystallization. After separation the optically active amines are can be hydrolyzed by standard means to form the following optical antipodes

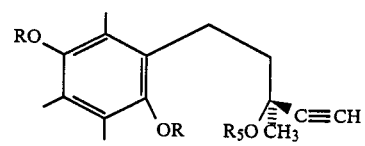      XI-A and

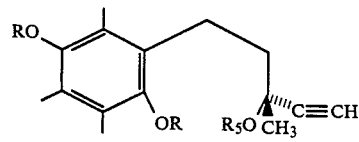      XI-B wherein R is as above and $R_5$ is

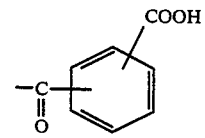

The compound of formula XI-A can be converted to the compound of formula V-A via the following intermediates

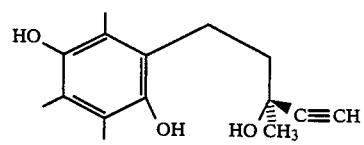      XII-A and

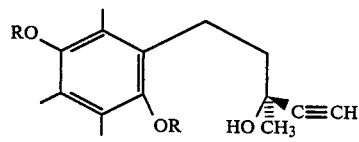      XIII-A wherein R is as above.

The compound of formula of XI-A is converted to the compound of the formula XII-A by conventional ester hydrolysis. The compound formula XII-A is converted to the compound of the formula XIII-A by esterification at low temperatures i.e. from −30° C. to room temperature. In carrying out this esterification it is generally preferred to utilize acid anhydrides and low temperatures such as −20° C. to 25° C. to avoid esterification of the tertiary hydroxy group. These conditions provide selective esterification.

The tertiary hydroxy group in the compound of formula XIII-A is next esterified with benzoic acid or a halo benzoic acid or reactive derivative thereof in the manner described hereinbefore to form the compound of formula V-A. In the same manner the compound of formula XI-B can be converted to the compound of formula V-B. In carrying out the spontaneous crystallization of the compound V into the compound the formula V-A or V-B, the compound XI-A or the compound of formula XI-B can be utilized to produce the seed, which is the compound of formula V-A or V-B, for use in this procedure, depending upon the desired isomer to be isolated.

The compound of formula V-A can be converted to natural optically active Vitamin E, the compound formula I-A, by first forming the compound of formula XII-A by conventional ester hydrolysis and then converting the compound of formula XII-A into compound formula I-A via the following intermediates

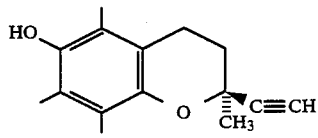

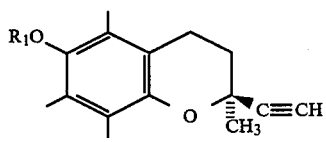

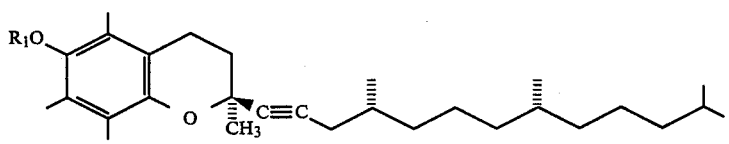

wherein $R_1$ taken together with its attached oxygen atom forms a hydrolyzable ether protecting group.

The compound of formula XII-A may be cyclized with complete retention of configuration and optical purity to the compound of formula IV-A in the manner described by Mayer, et al *Helv. Chim Acta*, Volume 7, pg 650–671 (1963). In accordance with this invention the compound of formula V-A can be cyclized with complete retention of optical configuration to the compound of formula IV-A in a one pot reaction by first forming the compound of formula XII-A by ester hydrolysis and then acidification of the reaction mixture with an inorganic acid such as sulfuric acid. If desired the conversion of the compound of formula V-A to the compound of formula IV-A can be catalyzed by the addition of a small amount of the optically active quinone of formula VI-A. The compound of formula IV-A is converted by etherification to the compound of formula XV-A utilizing conventional procedures. The compound of formula XV-A is next condensed with a compound of the formula:

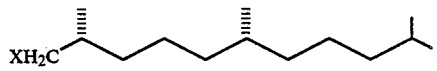

XVII wherein X is halo or leaving group to produce the compound of formula XVI-A. Any means of condensing an acetylenic compound with a halide can be utilized to carry out this process to react the compound of formula XV-A with the compound of formula XVII to produce the compound of formula XVI-A. The compound of formula XVI-A is converted to the compound of formula I-A by hydrogenation. An conventional method of hydrogenating a triple bond to a saturated bond can be utilized. Hydrogenation not only reduces the triple bond in the compound of formula I-A, it also removes the hydroxy ether protecting group.

In accordance with another embodiment of this invention. The compound of formula III is directly converted to the compound of formula VI which is then separated by spontaneous crystallization into its optical antipodes i.e. the compound of formula VI-A and VI-B. The compound of formula III can be converted to the compound of formula VI by oxidation. Any method conventional for oxidizing hydroquinones to quinones can be utilized for this produce. The compound of formula VI can be separated into its individual antipodes

IV-A

XV-A

XVI-A by spontaneous crystallization. This is accomplished by dissolving the compound of formula VI in an aromatic hydrocarbon solvent. In so doing, the optical antipodes are in a solution from which they can be separated. Any conventional method of separation, such as crystallization can be utilized to accomplish this.

Any conventional hydrocarbon solvent can be utilized, with toluene being preferred, to accomplish the separation of the optical antipode from said solution. Crystallization can be accomplished by conventional procedures, with the preferred technique being the seeding of the solution with a crystal of the desired optical antipode. Seeds of the compound of formula VI-A can be prepared by oxidizing the compound of formula XII-A in the manner disclosed in connection with the oxidation of the compound of formula III to the compound of formula VI. If the compound of formula VI-B is desired, the compound of formula VI-B can be prepared from the compound of V-B in like manner. The compound of formula VI-B can be used as a seed to crystallize the compound of formula VI-B from solution.

In converting the compound of formula VI-A to natural vitamin E, the compound of formula VI-A can be converted to the compound IV-A through the formation of formula XII-A as an intermediate. In this procedure the compound of VI-A is reduced to the compound of formula XII-A. Any conventional method of reducing a quinone to a hydroquinone can be utilized to convert the compound of formula VI-A to the compound of formula XII-A. Among the preferred reducing agents are zinc dust and the hydride reducing agents such as lithium aluminum hydride and sodium borohydride. The compound of formula XII-A can be converted to the compound of formula IV-A and to the compound of formula I-A as described hereinbefore.

In accordance with this invention the optical antipodes of formula V-A, V-B, VIA, VI-B, XI-A, XI-B, XII-A, XIII-A, IV-A, XV-A and XVI-A are produced in substantially pure form without substantial contamination of the other optical antipodes. In this manner optically pure natural vitamin E of the formula I-A can be produced, without substantial contamination of the other isomers of Vitamin E.

In accordance with this invention the compound of formula VI-B, the optical antipode different from natural vitamin A, can be utilized to product natural vitamin A by means of racemization or inversion of the compound of formula VI-B.

The compound of formula VI-B can be racemized to form the compound of formula VI by first converting the free hydroxy group in the compound of formula VI-B into a mesyloxy or tosyloxy group and thereafter hydrolyzing the mesyloxy or tosyloxy group from this compound to form the corresponding racemate of formula VI.

In forming the racemate of formula VI, the compound of formula VI-B is treated with tosylchloride, mesyl chloride or a reactive derivative of a lower alkanoic acid to form a compound of the formula

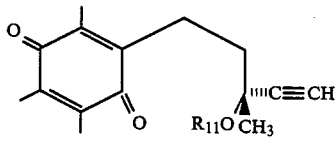

XX-B wherein $R_{11}$ is mesyl, tosyl or lower alkanoyl.

Any conventional method of converting a hydroxy group into a mesyloxy, tosyloxy or lower alkanoyloxy group can be utilized in producing the compound of formula XX-B from the compound of formula VI-B.

The compound of formula XX-B is converted to the racemate of formula VI by hydrolizing $OR_{11}$ from the compound of formula XX-B. Generally this hydrolysis is carried out under mild hydrolysis conditions in an aqueous medium, containing an inert organic solvent such as an ether solvent such as tetrahydrofuran, dioxane, etc. Any method of hydrolyzing mesyl, tosyl or lower alkanoyl to produce a corresponding hydroxy group can be utilized in carrying out this procedure. However it is generally preferred that the reaction be carried out in the aqueous medium utilizing a metal as a catalyst such as a silver, particularly silver having a valance of plus one. The compound of formula VI produced in this manner from the optical antipode of formula VI-B can thereafter be resolved into its optical antidote including the desired optical antipodes of formula VI-A.

On the other hand, the compound of formula XX-B can be inverted through reduction to form the compound of formula IV-A. In this procedure, the compound of formula XX-B is converted into the compound of formula

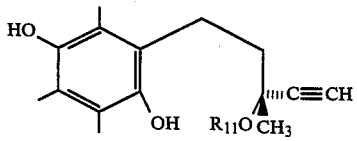

XXII-B wherein $R_{11}$ is as above by reduction. Any conventional method of reducing a quinone to a hydroquinone can be utilized to carry out this procedure. Among the preferred methods is by treating the compound of formula XX-B with zinc dust or an alklai metal hydride reducing agent such as sodiumborohydride, utilizing conditions conventional in such reductions. In this manner the compound formula XX-B can be directly converted to the compound of formula IV-A. In this reaction the compound of formula XXII-B is formed as a transitory intermediate which under the conditions of the reduction reaction cyclizes into the compound of formula IV-A. The presence of the lower alkanoyl, mesyloxy or tosyloxy group, in accordance with this invention, produces inversion. When $R_{11}$ is an lower alkanoyloxy group in the compound of formula XXII-B, cyclization preferably occurs to form the compound of formula VI-A in the presence of silver (I) as a catalyst. The silver (I) catalyst can also be utilized when $R_{11}$ is mesyl or tosyl.

In the same manner the compound of formula V-B can also be racemized to be a compound of formula V and be utilized to produce natural vitamin E having the formula I-A. This is accomplished by converting, as described herein, the compound of formula V-B into the compound of the formula V utilizing the same procedure for converting the compound of the formula VI-B to the compound of formula VI as described. The compound of formula IV-B can then be utilized in forming the compound of formula I-A as described above.

The invention is further illustrated by the following examples. These examples are illustrative but not limited of the claimed invention.

EXAMPLE 1

Rac-5-[2,5-Bis(acetyloxy)-3,4,6-trimethylphenyl]-3-methyl-1-pentyn-3-ol 17.6g (0.67 mol) if acetylene gas was collected into 350 mL of dry THF (tetrahydrofuran) at −78° C. in a three-necked flask equipped with mechanical stirrer and dropping funnel. to this solution, under agron, a solution of 387 mL (0.62 mol) of n-butyl lithium (1.6M in hexane) was added dropwise at such a rate that the internal temperature was maintained at −80° to −65° C. The solution was then added dropwise, at −70° C., 64.33 g (0.21 mol) of 4-(2,5-diacetyloxy)-3,4,6-trimethylphenyl-butan-2-one in 300 mL of dry THF, over a period of 45 min. The reaction mixture was mechanically stirred at −70° C. for 1.0 h, and then the dry ice-acetone bath was removed. When the temperature of the reaction mixture reached −30° C., 500 mL of water was added dropwise very slowly, followed by addition of 50 g of ammonium chloride. The mixture was then degassed with nitrogen, and allowed to come to 25° C. After approximately 30 min. the mixture was extracted with 2×500 mL ether. The combined organic extracts were dried over anhydrous MgSO₄, filtered, and concentrated in vacuo to give 76 g of yellow oil. This material was dissolved in 25 mL of CH₂Cl₂, and 25 mL of ether at 30° C. Then 125 mL of hexane was added, and the solution was seeded, and refrigerated at about 4° C. for 18 h. The resulting solid was collected, washed with 100 mL of cold ether, air dried first, and again dried at 25° C./1.0 mm for 20 h to yield 54.9 g of rac-5-[2,5-bis(acetyloxy)-3,4,6-trimethylphenyl]-3-methyl-1-pentyn-3ol as a white solid, mp 116°–118° C., (softens at 96° C.). The mother liquor was concentrated in vacuo to give 19 g of the titled compound as a yellow oil, which was crystallized as described above from CH₂Cl₂/ether/hexane (5 mL, and 50 mL respectively) to give a second crop of 13.3 g of titled compound as a white solid. The total yield of the titled compound 68.2 g (97% yield).

EXAMPLE 2

Rac-1,2-Benzenedicarboxylic acid [3-[2,5-bis (acetyloxy)-3,4,6-trimethylphenyl]-1-ethynyl-1-methylpropyl]ester A mixture of 21.25 g (0.064 mol) of (rac.-5-[2,5-bis-(acetyloxy-3,4,6-trimethylphenyl]-3-methyl-1-pentyn-3-ol), 12.12 g (0.12 mol) of triethylamine, 2.44 g (0.02 mol) of 4-dimethylaminopyridine, and 11.84 g (0.08 mol) of phthalic anhydride in 100 mL of dichloromethane was stirred at 25° C. for 3.0 h, then heated under reflux for 10 h. The reaction mixture was cooled to 25° C. and diluted with 200 mL of diethylether. The solution was washed with 3×150 mL of 1.0 N HCl. The aqueous phase was further extracted with 2×200 mL of diethylether. The organic phase were combined and extracted with 3×100 mL of 1.0 N ammonium hydroxide. The basic aqueous extracts were combined, cooled in an ice-bath, and acidified carefully to pH 5.0 with approximately 60 mL of cold 6.0 N HCl. It was then extracted with 4×200 mL of dichloromethane. The combined extracts were dried over MgSO$_4$. Filtration and solvent removal on a rotary evaporator (35° C., 40 mm) gave a light yellow oily residue. This material was transferred to a flask with about 100 mL of diethylether, and the solvent was evaporated as described above to give a foam, which was further dried at 25° C./0.5 mm for 18 h to yield 31 g of rac.-benzenedicarboxylic acid [3-[2,5-bis (acetyloxy)-3,4,6-trimethylphenyl]-1-ethynyl-1-methylpropyl] ester as a pale yellow foam.

EXAMPLE 3

Racemic-Benzoic Acid [3-[2,5-bis(acetyloxy)-3,4,5-trimethylphenyl]-1-ethynyl-1-methylpropyl]ester A mixture of 25 g (0.075 mmol) rac-5-[2,5-bis-(acetyloxy)-3,4,6trimethylphenyl]-3-methyl-1-pentyn-3-ol, 9.1 g (0.075 mmol) of dimethylamino pyridine, 12.5 g (0.125 mmol) of benzoyl chloride, and 10 mL of triethylamine, in 100 mL of CH$_2$Cl$_2$ was refluxed for 16 h. It was cooled to 25° C. and taken into ether and washed with 3×200 mL cold 1.0 N HCl, 2×200 mL cold saturated NaHCO$_3$, and 2×200 mL water. The aqueous phase, were further back extracted with 2×200 mL ether. The combined ether phases were dried over MgSO$_4$, filtered, and concentrated in vacuo to yield 35.3 g of tan oil. The oil was dissolved in 75 mL of hot toluene, and 125 mL of hexane added. Crystallization occurred quickly at 25° C. and the resulting crystals were collected, dried in vacuo to give 31 g of racemic-benzoic acid [3-[2,5-bis(acetyloxy)-3,4,5-trimethylphenyl]-1-ethynyl-1-methylpropyl]ester as white solid (95%): mp 132°–138° C.

EXAMPLE 4

Spontaneous Resolution of Racemic-Benzoic Acid [3-[2,5-bis(acetyloxy)-3,4,5-trimethylphenyl]-1ethynyl-1-methylpropyl]ester 1. 5.1 g of rac-benzoic acid [3-[2,5-bis (acetyloxy)-3,4,5-trimethylphenyl]-1-ethynyl-1-methylpropyl]ester (~4.5% optical purity enriched with (S)-(−)-Benzoic acid [3-[2,5-bis(acetyloxy)-3,4,6-trimethylphenyl]-1-ethynyl-1-methylpropyl]ester (Example 19) was dissolved in 20 g of toluene at 35° C. (Concentration C=0.25 g/g of toluene). The resulting solution was stirred mechanically and then seeded with 5 mg of the optically pure (S)-(−)-Benzoic acid [3-[2,5-bis (acetyloxy)-3,4,6-trimethylphenyl]-1-ethynyl-1-methylpropyl]ester at 30° C. The mixture was allowed to equilibrate to 20° C. over 0.5 h. The white crystals were collected by filtration, and dried in vacuo at 25° C. to yield 310 mg of (S)-(−)-Benzoic acid [3-[2,5-bis(acetyloxy)-3,4,6-trimethylphenyl]-1-ethynyl-1-methylpropyl]ester, $[\alpha]_D^{25} -11.37°$ (c 1, CHCl$_3$). The optical purity was about 67% by comparison with the $[\alpha]_D^{25} -17.5°$ (CHCl$_3$) of an optically pure material.

2. To start cycle 2, racemic-benzoic acid [3-[2,5-bis(acetyloxy)-3,4,5-trimethylphenyl]-1-ethynyl-1-methylpropyl]ester (310 mg) was added to the mother liquor along with 0.5 mL of toluene so that the total weight of crystals and toluene was approximately 25 g (~0.25 g/g of toluene). The reaction was warmed to 35° C. and all crystals dissolved. The resulting solution was stirred mechanically and was seeded with 5 mg of the optically pure (R)-(+)-benzoic acid [3-[2,5-bis(acetyloxy)-3,4,6-trimethylphenyl]-1-ethynyl-1-methylpropyl] ester at 30° C. The resulting mixture was allowed to equilbrate to 15° C. over 0.5 h. The resulting white crystals were collected, dried in vacuo to give 320 mg of (R)-(+)-benzoic acid [3-[2,5-bis(acetyloxy)-3,4,6-trimethylphenyl]-1-ethynyl-1-methylpropyl]ester, $[\alpha]_D^{25} +5.97$ (CHCl$_3$)

3. Cycles 3 through 10 were carried out as described above.

4. All of (S)-(−)-crystals (from cycles 1, 3, 5, 7, 9) were combined to yield 2.24 g of (S)-(−)-Benzoic acid [3-[2,5-bis(acetyloxy)-3,4,6-trimethylphenyl]-1-ethynyl-1-methylpropyl]ester having 38% optical purity. All R-(+) crystals (cycles 2, 4, 6, 8, 10) were combined to give 2.49 g of (R)-(+)-benzoic acid [3-[2,5-bis(acetyloxy)-3,4,6-trimethylphenyl]-1-methylpropyl]ester having 29% optical purity. The racemic benzoate added in all cycles was 4.74 g plus 5.1 g at start for a total of 9.84 g.

5. The ((S)-(−) benzoate, i.e.(S)-(−)-benzoic acid [3-[2,5-bis(acetyloxy)-3,4,6-trimethylphenyl]-1-ethynyl-1-methylpropyl] ester (2.24 g 38% optical purity was dissolved in 10 g of warm toluene (35° C. bath). The solution was mechanically stirred at ~75 rpm and was seeded with 5 mg of optically pure (S)-(−) benzoate. It was cooled to 25° C. over 1 h. The crystals were collected by filtration and dried to yield 1.05 g of (S)-(−)-benzoic acid [3-[2,5-bis(acetyloxy)-3,4,6-trimethylphenyl]-1-ethynyl-1-methylpropyl]ester as white crystals: $[\alpha]_D^{25} -15.15$ (CHCl$_3$). The material was further recrystallized as above from 3.3 g of warm toluene in the same manner as above to give 890 mg of (S)-(−)-benzoic acid [3-[2,5-bis (acetyloxy)-3,4,6-trimethylphenyl]-1-ethynyl-1-methylpropyl] ester as white crystals: mp 152°–154° C., $[\alpha]_D^{25} -16.19$ (c, 0.68, CHCl$_3$).

6. In the same manner as described above, the (R)-(+) benzoate, i.e. (R)-(+)-benzoic acid [3-[2,5-bis-(acetyloxy)-3,4,6-trimethylphenyl]-1-ethynyl-1methylpropyl]ester (2.49 g, 29% optically pure) was recrystallized form 10 g of toluene to yield 1.34 g of white crystals: $[\alpha]_D^{25} +11.93$ (CHCl$_3$). Recrystallization of this material from 4.1 g of warm toluene yielded 885 mg of (R)-(+)-benzoic acid [3-[2,5-bis(acetyloxy)-3,4,6-trimethylphenyl]-1-ethynyl-1-methylpropyl]ester as white crystals: mp 151°–153° C., $[\alpha]_D^{25} +17.11°$ (CHCl$_3$).

EXAMPLE 5

S-(+)-2-[3-Hydroxy-3-Methyl-4-pentynyl]-3,5,6Trimethyl-2,5-Cyclohexadiene-1,4 dione A solution of 100 mg (0.229 mmol) of (S)-(−)-benzoic acid [3-[2,5-bis(acetyloxy)-3,4,6-trimethylphenyl]-1-ethynyl-1-methyl propyl]ester (from spontaneous resolution of Example 4), 3 mL of methanol and 1 mL 6N NaOH was refluxed at 80° C. for 1h. The reaction mixture was cooled to 0° C. and taken into 100 mL water and acidified (pH 5.0) with ~1mL 5.6 N $H_2SO_4$. It was extracted with 2×100 mL ether then washed with 2×100 mL saturated sodium bicarbonate and 100 mL water. Ether phases were dried over $MgSO_4$, filtered, and concentrated in vacuo to near dryness. To this was added portionwise over 2 h (2 mL every 20 min) a solution of 500 mg ferric chloride in 12 mL methanol/water (1/1). The mixture was stirred at 25° for 16 h. it was taken into water and extracted with 2×100 ether, washed with 2×100 mL water, dried over $MgSO_4$, filtered and concentrated in vacuo. S-(+)-2-[3-Hydroxy-3-methyl-4pentynyl]-3,5,6-trimethyl-2,5cyclohexadiene-1,4-dione e was isolated (20 mg) by a thick layer TLC on silica gel with ether/hexane (3:7) as yellow crystals (35.4%), shown to be optically pure by NMR.

EXAMPLE 6

R-(−)-2-[3-Hydroxy-3-Methyl-4-pentynyl]-3,5,6 Trimethyl-2,5-Cyclohexadiene-1,4-dione A solution of 100 mg (0.229 mmol) (R)-(+)-benzoic acid [3-[2,5-bis(acetyloxy)-3,4,6-trimethylphenyl]-1-ethynyl-1-methyl - propyl]ester (from spontaneous resolution of Example 4), 3 mL of methanol and 1 mL 6N NaOH was refluxed at 80° C. for 1 h. The reaction mixture was cooled to 0° C. and taken into 100 mL water and acidified to pH 5.0 with ~1mL 5.6 n $H_2SO_4$. It was extracted with 2×100 mL ether then washed with 2×100 mL saturated sodium bicarbonate and 100 mL water. Ether phases were dried over $MgSO_4$, filtered, and concentrated in vacuo to near dryness. To this was added portionwise over 2 h (2 mL every 20 min) 500 mg ferric chloride in 12 mL methanol/water (1/1). It was stirred at 25° C. for 16 h, taken into 100 mL water and was extracted with 3×100 mL ether. The combined ether extracts were washed with 2×100 mL water, dried over $MgSO_4$, filtered, and concentrated. The quinone was isolated by a thick layer TLC ether/hexane (3:7) to give 16 mg of (R)-(−)-2-[3-hydroxy-3-methyl-4-pentynyl]-3,5,6-trimethyl-2,5-cyclohexadiene-1,4-dione as a yellow solid (28.3%), shown to be optically pure by NMR.

EXAMPLE 7

(S)-1,2-Benzenedicarboxylic acid[3-[2,5-bis(acetyloxy)-3,4,6-trimethylphenyl]-1-ethynyl-1-methylpropyl]ester (S) -α-methylbenzenemethanamine (1:1) (salt)

To a solution of 27.00 g (0.056 mol) of rac-1,2-benzenedicarboxylic acid [3-[2,5-bis(acetyloxy)-3,4,6-trimethylphenyl]-1-ethynyl-1-methylpropyl]ester in 50 mL of 95% ethanol was added, with stirring 7.02 (0.058 mol) of (S)-(−)-α-methylbenzylamine in 250 mL of diethylether. The resulting solution was stirred at 25° C. for 0.5 h, then cooled in an ice bath until crystallization occured. It was further stirred at 0° C. for 0.5 h and the crystals were collected and air dried to give 16 g of white solid. This white solid was dissolved in 50 mL of ethanol (95%) and 150 mL of diethylether. The solution was kept at 25° C. for approximately 1.0 h and crystallization occurred. It was further stored at 0° C. for 1.0 h and the crystals were collected, dried at 25° C./0.5 mm for 24 h to yield 10.1 g of (S)-1,2-benzenedicarboxylic acid[3-[2,5-bis(acetyloxy)-3,4,6-trimethylphenyl]-1-ethynyl-1-methylpropyl]ester(S)-α-methyl benzenemethanamine (1:1) (salt) as a white solid (30% yield from racemic starting materials), m.p. 162°–165 C.

The mother liquor from this crystallization of the white solid was evaporated to dryness and the residue was used in Example 8.

EXAMPLE 8

(R)-1,2-Benzenedicarboxylic acid[3-2,5-bis(acetyloxy)-3,4,6-trimethylphenyl]-1-ethynyl-1-methylpropyl]ester(R)-α-methyl benzenemethanamine (1:1) (salt)

The recovered mother liquor from Example 7 was evaporated to give an oily residue which was taken into 100 mL of diethylether and treated with 100 mL of 1.0 N HCl. The mixture was stirred vigorously for 0.5 h. The ether layer was separated and further washed with 2×100 mL =200 mL of 1.0 N HCl, and 100 mL of water. The aqueous phase was back extracted with 100 mL of diethylether. The ether extracts were combined, dried over $MgSO_4$, and filtered. To this etheral filtrate was added 50 mL of 95% ethanol, followed by 5.2 g (0.043 mol) of (R)-(+)-α-methylbenzylamine. The solution was stirred at 0° C. for 1.0 h and the resulting crystalline substance was collected by filtration to give approximately 18 g of white solid. It was recrystallized from 50 mL of ethanol and 150 of diethylether (as described in Example 7) to give 11.04 g of (R)-1,2-benzenedicarboxylic acid[3-[2,5-bis(acetyloxy)-3,4,6-trimethylphenyl]1-ethynyl-1-methylpropyl]ester(R)-α-methyl benzenemethanamine (1:1) (salt) as a white solid (32.8% yield); mp 163°–166° C., $[\alpha]_D^{25}$ +9.6° (c=1.03, $C_2H_5OH$).

EXAMPLE 9

(S)-(+)-1,2-Benzenedicarboxylic acid[3-[2,5-bis(acetyloxy)-3,4,6-trimethylphenyl]-1-ethynyl-1methylpropyl]ester A mixture of (S)-1,2-benzenedicarboxylic acid[2,5-bis(acetyloxy)-3,4,6-trimethylphenyl]-1-ethynyl-1methylpropyl] ester-(S)-α-methyl benzenemethanamine (1:1) (salt) (110 g, 0.17 mol), 400 mL of 1.0 N HCl, and 40 mL of $CH_2Cl_2$-ether (1:9) was stirred vigorously for 1.0 h at 25° C. It was then extracted with ether (2×200mL). The ether extracts were combined, washed with 1.0 N HCl (200 mL), water (200 mL), and dried over anhydrous MgSO4. Evaporation of ether in vacuo gave a solid which was further dried at 25° C./0.5 mm for 16 h to afford 80.59 of (S)-1,2-benzenedicarboxylic acid [3-[2,5-bis(acetyloxy)-3,4,6-trimethylphenyl]-1-ethynyl-1-methylpropyl]ester as a white foam: $[\alpha]_D^{25}$+15.95° (c 0.96, ethanol).

EXAMPLE 10

(R)-(−)-1,2-Benzenedicarboxylic acid[2,5-bis(acetyloxy)-3,4,6-trimethylphenyl]-1-ethynyl-1-methylpropyl]ester The title compound was prepared from (R)-1,2-Benzenedicarboxylic acid[3-[2,5-bis (acetyloxy)-3,4,6-trimethylphenyl]-1-ethynyl-1-methylpropyl]ester (R)-α-methyl benzenemethanamine (1:1) (salt) by the procedure described in Example 9. The product was a white foam: $[\alpha]_D^{25} -15.98°$ (ethanol).

EXAMPLE 11

(S)-(+)-5-[2,5-bis(acetyloxy)-3,4,6-trimethylphenyl]-3-methyl-1-pentyn-3-ol

A solution of 600 mg (1.25 mmol) of (S)-(+)-1,2-benzenedicarboxylic acid[3-[2,5-bis(acetyloxy)-3,4,6-trimethylphenyl]-1-ethynyl-1-methylpropyl]ester (Example 9) in 10 mL of methanol and 10 mL of 1.0 N NaOH was degassed with argon, and heated under reflux for 1.0 h. It was cooled to 0° C. and treated with 100 mL of cold 1.0 N HCl. It was then extracted with ether (3×100 mL). The extracts were combined, washed with saturated sodium bicarbonate solution (3×100 mL) dried over MgSO4, and filtered. Dry pyridine (1 mL) was added to the filtrate which was concentrated to near dryness at reduced pressure. The residue was cooled to 0° C. and treated with 3 mL of dry pyridine and 3 mL of acetic anhydride. The resultant solution was kept under argon at 0° C. for 3.0 h, then taken into 100 mL of cold 1 N HCl. It was then extracted with ether (3×100 mL). The ether extracts were combined, washed with cold 1.0 N HCl (2×100 mL), saturated sodium bicarbonate solution (3×100), brine (1×100 mL), and dried over MgSO4. The crude product (369 mg) was crystallized twice from ether-hexane (1:2) to give (S)-(+)-5-[2,5-bis(acetyloxy)-3,4,6-trimethylphenyl[-3-methyl-1-pentyn-3-ol as a white solid (114 mg): mp 96°-102° C., $[\alpha]_D^{25} +14.30°$ (c 0.956, ethanol): $[\alpha]_D^{25} +17.17°$ (CHCl3).

EXAMPLE 12

(R)-(−)-5-[2,5-bis(acetyloxy)-3,4,6-trimethylphenyl]-3-methyl-1-pentyn-3-ol

By the same procedure as described above (example 11), this compound was prepared from (R)-1,2-benzenedicarboxylic acid[3-[2,5-bis(acetyloxy)-3,4,6-trimethylphenyl]-1-ethynyl-1-methylpropyl]ester, as white crystals =mp 100°-103 C., $[\alpha]_D^{25} -17.38°$ (CHCl3).

EXAMPLE 13

Rac-2-[3-Hydroxy-3-methyl-4-pentynyl]-3,5,6-trimethyl-2,5-cyclohexadiene-1,4-dione A mixture of 200 g (0.6 mol) of racemic 5-[2,5-bis-(acetyloxy)-3,4,6-trimethylphenyl]-3-methyl-1-pentyn-3-ol. in 600 mL of methanol and 330 mL of 6N NaOH (1.98 mol) was refluxed at 80° C. (bath temperature) with stirring under argon for 1.0 h. It was cooled to ~4° C. and acidified to pH 5.0 with approximately 150 mL of 5.5 N H2SO4, and diluted with 300 mL of water. The mixture was extracted with 3×1.0 L ether. The ether extracts were washed with 500 mL saturated NaHCO3, and with 500 mL water, dried over anhydrous MgSO4, filtered, and concentrated in vacuo to near dryness. The resulting residue was transferred to a round bottom flask with approximately 200 mL ether. To this solution, with stirring was then added portionwise (250 mL each 15 min), 530 g (1.98 mol) of ferric chloride in 1.5 L of water/methanol (1:1) over a period of 90 minutes. The reaction mixture was stirred at 23° C. for 1.0 h, diluted with 1.0 L water, and extracted with 3×750 mL water, dried over anhydrous MgSO4. The mixture was filtered through a short column of 500 g of florisil and further washed with 750 mL ether. Concentration of ether in vacuo gave 162 g of red-orange oil, which was dissolved in 200 mL of ether and 900 mL of hexane was added portionwise. After storage at 4° C., the resulting yellow crystals were collected and washed with ~500 mL hexane, dried at 23° C. in vacuo to yield 114 g of rac-2[3-hydroxy-3-methyl-4-pentynyl]-3,5,6-trimethyl-2,5-cyclohexadeine-1,4-dione (77% yield), mp 61°-65° C. $[\alpha]_D^{25} 0.00$ (c 1.63, CH2Cl2). 15.2g (10.3%) of this product was also obtained from the mother liquor by crystallization.

EXAMPLE 14

Spontaneous Resolution of rac.-2-[3-Hydroxy-3-methyl-4-pentynyl]-3,5,6-trimethyl-2,5-cyclohexadiene-1,4-dione 1. 54.9 of rac.-2-[3-hydroxy-3-methyl-4-pentynyl]3,5,6-trimethyl-2,5-cyclohexadiene-1,4-dione (5.3% enriched with the S-(+) enantiomer) was dissolved in 108 g (125 mL) of toluene (0.51 g of compound per gram of toluene). The resulting yellow solution was stirred mechanically at approximately 60-90 rpm and the solution was allowed to equilbrate to 15° C. in a cold bath. The solution was seeded with 20 mg of -(S)-(+)-2-[3-hydroxy-3-methyl-4-pentynyl]-3,5,6-trimethyl-2,5-cyclohexadiene-1,4-dione, stirred at 15° to 5° C. for 10 min., and at 5° to 0° C. for 30 min. The yellow crystals were collected by filtration and dried in vacuo to give 8.46 g of the S-(+)quinone, $[\alpha]_D^{25} 9.27$ (C, 1.11, CH2Cl2). The optical purity was 81% by comparison with $[\alpha]_D^{25} +11.39°$ (CH2Cl2) of a 100% pure sample.

2. To start cycle 2, rac.-2-[3-hydroxy-3-methyl-4-pentynyl]-3,5,6-trimethyl-2,5-cyclohexadiene-1,4-dione (10 g) was added to the mother liquor from step (1), together with 2 mL of toluene so that the total weight of crystals and toluene was approximately 160 g. The resulting yellow solution was cooled to 15° C. with stirring at about 75 rpm. It was seeded with 20 mg of pure (R)-(−)-quinone, i.e. (R)-(−)-2-[3-hydroxy-3-methyl-4-pentynyl]-3,5,6-trimethyl-2,5-cyclohexadiene-1,4-dione, and processed in the same way as described in step (1). The crystals were collected and dried in vacuo to give 10.2 g of R-(−)-quinone $[\alpha]_D^{25} -8.72°$ (CH2Cl2). The optical purity was about 74% by comparison of the $[\alpha]_D^{25} -11.7°$ (CH2Cl2) of an optically pure sample.

3. Cycles 3 through 12 were carried out essentially in the same way as above for step (1) and (2).. In each cycle the weight of crystals and toluene was kept at 160 g compensating for the lose of solvent, and crystals removed.

4. All S-(+)-"crystals" (cycles 1,3,5,7,9,11) were combined to yield 52.49 g of (S)-(+)-2-[3-hydroxy-3-methyl-4-pentynyl]-3,5,6-trimethyl-2,5-cyclohexadiene-1,4-dione having 74.5% optically purity.

All R-(−)-"crystals" (cycles 2,4,6,8,10,12) were combined to give 51.21 g of (R)-(−)-2-[3-hydroxy-3-methyl-4-pentynyl]-3,5,6-trimethyl-2,5-cyclohexadiene-1,4-dione having 73% optically purity.

5. The S-(+)-quinone (52.49 g, 74.5% optical purity) from step (4) was dissolved in 125 mL of toluene (warmed gently on a steam bath), and then was seeded with 20 mg of the optically pure S-(+)-quinone at 25° C. The mixture was stirred at 75 rpm for 30 min (temperature was 25° C.-15° C.) in a cooled bath. The crystals were collected by filtration, washed with cold toluene (100 mL), and dried at 25° C. in vacuo for 20 hr to yield 27.5 g of S-(+)-quinone, mp 78°-82° C., $[\alpha]_D^{25}+10.78°$ (C, 1.4, CH$_2$Cl$_2$). This material was further recrystallized form 70 mL of toluene in the same manner as described above to give 15.62 g of (S)-(+)-2-[3-hydroxy-3-methyl-4-pentynyl]-3,5,6-trimethyl-2,5-cyclohexadiene-1,4-dione, as yellow rods, mp 80°–82° C., $[\alpha]_D^{25}+11.32°$ (CH$_2$Cl$_2$). NMR showed no R-(−)-quinone present. The mother liquor was evaporated to give 12 g of material which was recrystallized from 30 mL of toluene to give another 5.04 of S-(+)-quinone, mp 79°–82.5° C., $[\alpha]_D^{25}+11.21°$. The total yield of optically pure S-(+)-quinone was, therefore, 20.66 g (13% yield of optically pure (S)-(+)-2-[3-hydroxy-3-methyl-4-pentynyl]-3,5,6-trimethyl-2,5-cyclohexadiene-1,4-dione from 158.9 g of racemic rac.-2-[3-hydroxy-3-methyl-4-pentynyl]3,5,6-trimethyl-2,5-cyclohexadiene-1,4-dione.

6. In the same manner as described in step (5), the R-(−)-quinone (51.21 g, ~73% optical purity) was recrystallized from 125 mL of toluene to yield 23.4 g of R-(−)-quinone, as yellow rods, mp 76°–82° C., $[\alpha]_D^{25}-11.1°$ (C, 1.04 CH$_2$Cl$_2$), no S-(+)-enantiomer was detected by NMR. A second crop (2.66 g) was also obtained as yellow needled =78°–8.51° C., $[\alpha]_D^{25}-11.37°$ (C, 0.87, CH$_2$Cl$_2$). NMR showed no S-(+)-enantiomer present. Therefore, the total yield of optically pure R-(−)-quinone, i.e. (R)-(−)-2-[3-hydroxy-3-methyl-4-pentynyl]-3,5,6-trimethyl-2,5-cyclohexadiene-1,4-dione was 17.99 g (11.32% of optically pure (R)-(−)-2-[3-hydroxy-3-methyl-4-pentynyl]-3,5,6-trimethyl-2,5-cyclohexadiene-1,4dione from 158.9 g of rac.-2-[3-hydroxy-3-methyl-4-pentynyl]-3,5,6-trimethyl-2,5-cyclohexadiene-1,4-dione.

EXAMPLE 15

S-(+)-2-[3-Hydroxy-3-methyl-4-pentynyl-3,5,6-trimethyl-2,5-cyclohexadiene-1,4-dione To a solution of 21.0 g (0.44 mol) of (S)-(+)-1,2-benzenedicarboxylic acid [3-[2,5-bis(acetyloxy)-3,4,6-trimethylphenyl]-1-ethynyl-1-methylpropyl]ester (example 9) in 50 mL of methanol was added 43 mL (0.26 mol) of 6N NaOH. The reaction mixture was heated at 80°–85° C. (bath) with stirring under argon for 1.0 h. It was cooled in an ice bath and approximately 22 mL of 5.0 N H$_2$SO$_4$ was added dropwise so that the final pH was about 5–5.5. The mixture was extracted with 3×200 mL ether. The combined ether extracts were 3×200 mL washed with 3×200 mL water, and dried over anhydrous MgSO$_4$. It was filtered through a short column of 100 g of florisil, and further washed with 400 mL of ether. The ether solution was than concentrated to approximately 100 mL. To this solution with stirring, was then added portionwise over a period of 2.0 h, (25 mL portions in every 20 min) 24g of ferric chloride (0.09 mol) in 150 mL of water-methanol (1:1). The reaction mixture was stirred at 25° C. for 1.0 h, and taken into 200 mL ether, washed with 4×200 mL water, and back extracted with 2×200 mL ether. The combined ether extracts were dried over anhydrous MgSO$_4$, filtered, and concentrated to give 10.3 g of orange-brown oil. This was dissolved in 50 mL of ether and 70 mL of hexane was added. After several hours at 23° C., the resulting yellow crystals were collected, washed with hexane, and dried in vacuo to give 4.77 g of (S)-2-[3-hydroxy-3-methyl-4-pentynyl]-3,5,6-trimethyl-2,5-cyclohexadiene-1,4-dione as yellow needles, mp 79°–82° C., optically pure by NMR, $[\alpha]_D^{25}+11.32°$ (CH$_2$Cl$_2$).

The mother liquor (5.6 g) from the above crystallization was purified by preparative HPLC on silica gel, and elution with ether/hexane (2:3) gave 3.5 g of yellow oil. This was crystallized from 10 mL of ether and 20 mL of hexane to give 2.53 g of yellow needles, mp 80°–82° C., optically pure by NMR. The total yield was, therefore, 7.3g (67.5%).

EXAMPLE 16

R-(−)-2-[3-Hydroxy-3-methyl-4-pentynyl]-3,5,6-trimethyl-2,5-cyclohexadiene-1,4-dione 23.9 g (0.05 mol) of (R)-(−)-1,2-benzenedicarboxylic acid [3-[2,5-bis(acetyloxy)-3,4,6-trimethylphenyl]-1-ethynyl-1-methylpropyl]ester (example 10) in 50 mL of methanol and 50 mL of 6N NaOH (0.3 mol) were heated at 80° C. (Bath) for 1.0 h. It was worked up as described in Example 14. The resulting solution containing the crude hydroquinone solution in 100 mL of ether was treated portionwise with (50 mL every 20 min) of ferric chloride 30 g (0.11 mol) in 200 mL of water/methanol (1:1) over a period of 80 min. The reaction mixture was worked up in the same manner as described in the Example 14 to give 12.9 g of orange oil. This was taken into 50 mL of ether and 75 mL of hexane. After several hours at 23° C., the resulting yellow crystals were collected, washed with hexane, and dried in vacuo to give 6.2 g of (R)-(−)-2-[3-hydroxy-3-methyl-4-pentynyl]-3,5,6-trimethyl-2,5-cyclohexadiene-1,4-dione as yellow needles, mp 79°–82° C., $[\alpha]_D^{25}-11.99°$ (C, 1.085, CH$_2$Cl$_2$). An additional of amount of product 3.97 g was obtained after purification of the mother liquor by HPLC and crystallization, mp 78°–81° C., optically pure by NMR. The total yield was, therefore, 10.17 g (83%).

EXAMPLE 17

S-(+)-5-[2,5-Bis(acetyloxy)-3,4,6-trimethylphenyl]-3-methyl-1-pentyn-3-ol

A mixture of 3.0 g (12.2 mmol) of S-(+)-2-[3-hydroxy-3-methyl-4-pentynyl]-3,5,6-trimethyl-2,5-cyclohexadiene-1,4-dione, and 3.0 g of zinc dust in 15 mL of acetic anhydride, and 1 mL of dry pyridine was stirred at 0° C. for 1.0 h. It was filtered and worked up with ether in the unusual manner to give the crude product. Purification by HPLC (silica gel, ether-hexane 3:2) followed by crystallization afforded 2.83 g of S-(+)-5-[2,5-bis-(acetyloxy)-3,4,6-trimethylpenyl]-3-methyl-1-pentyn-3ol, identical with a reference sample from example 11. as a white solid: $[\alpha]_D^{25}+17.1°$ (CHCl$_3$).

EXAMPLE 18

(R)-(−)-5-[2,5-Bis(acetyloxy)-3,4,6-trimethylphenyl]-3-methyl-1-pentyn-3ol

By the same procedure described in Example 17, the title compound was prepared form (R)-2-[3-hydroxy-3-methyl-4-pentynyl]-3,5,6-trimethyl-2,5-cyclohexadiene-1,4-dione, mp 100°–103° C. (from ether-hexane): $[\alpha]_D^{25}+14.38°$ (C$_2$H$_5$OH): $[\alpha]_D^{25}-17.38°$ (CHCl$_3$).

EXAMPLE 19

Preparation of (S)-(−)-Benzoic Acid [3-[2,5-bis(Acetyloxy)-3,4,6-Trimethylphenyl]1-ethynyl-1-methylpropyl]ester A mixture of 500 mg (1.5 mmol) S-(+)-5-]2,5-bis-(acetyloxy)-3,4,6-trimethylphenyl]-3-methyl-1-pentyn-3-ol, (example 11) 183 mg (1.5 mmol) dimethylaminopridine and 250 mg (2.5 mmol) benzoyl chloride in 10 mL dry toluene and 2 mL trimethylamine was heated (bath 110° C.) for 24 h. It was cooled to 25° C. and taken into 100 mL of ether and washed with 3×100 mL cold 1.0N HCl 3×100 ml cold saturated sodium bicarbonate 100 mL water. The combined ether phases were dried over MgSO$_4$, filtered and concentrated in vacuo to yield 830 mg of yellow solid, which was crystallized from 1 mL toluene to yield 587 mg of (S)-(−)-benzoic acid [3-[2,5-bis(acetyloxy)-3,4,6-trimethylphenyl]-1-ethynyl-1-methylpropyl]ester as white crystals (89.6%): mp 149°–153° C., $[\alpha]_D^{25} -17.05°$ (c 0.68, CHCl$_3$).

EXAMPLE 20

(R)-(+)-Benzoic Acid [3-[2,5-bis(Acetyloxy)-3,4,6-Trimethylphenyl]1-Ethynyl-1-Methylpropyl]ester A mixture of 500 mg (1.5 mmol) (R)-(−)-5-[2,5-bis-(acetyloxy)-3,4,6-trimethylphenyl]-3-methyl-1-pentyn-3-ol, 183 mg (1.5 mmol) dimethylaminopyridine and 250 mg (2.5 mmol) benzoylchloride in 10 mL dry toluene and 2 mL trimethylamine was heated (bath 110° C.) for 24 h. It was cooled to 25° C. and taken into 100 mL of ether and washed with 3×100 mL cold 1.0 N HCl 3×100 mL cold saturated sodium bicarbonate and 100 mL water. All washes were back extracted with 100 mL ether. The combined ether phases were washed with water, dried over MgSO$_4$, filtered and concentrated in vacuo to yield 775 mg of yellow solid, which was crystallized from 1 mL toluene to yield 431 mg of (R)-(+)-benzoic acid [3-[2,5-bis(acetyloxy)-3,4,6-trimethylphenyl]-1-ethynyl-1-methylpropyl]ester as white crystals (66%): mp 148°–152° C., $[\alpha]_D^{25} +17.24°$ (CHCl$_3$).

EXAMPLE 21

(S)-2-[3-(Acetyloxy)-3-methyl-4-pentynyl]-3,5,6-trimethyl-2,5-cyclohexadiene-1,4-dione A mixture of 1.23 g (5 mmol) of (S)-2-[3-hydroxy-3-methyl-4-pentynyl]-3,5,6-trimethyl-2,5-cyclohexadiene-1,4-dione ($[\alpha]_D^{25} +11.3°$ CH$_2$Cl$_2$), 1.05 mL of triethylamine, 120 mg of 4-N,N-dimethylamino pyridine, and 0.6 mL of acetic anhydride in 8 mL of CH$_2$CL$_2$ was stirred at 25° C. under argon for 17 h. It was diluted with CH$_2$CL$_2$ (70 mL), washed with 1.0 N HCl, saturated NaHCO$_3$ solution, water and dried over MgSO$_4$. The crude material (1.6 g) was purified by flash chromatography on silica gol (50 g; 230–400 mesh). Elution with ether:petroleum ether (3:17) gave 1.47 g of (S)-2-[3-(acetyloxy)-3-methyl-4-pentynyl]-3,5,6-trimethyl-2,5-cyclohexadiene-1,4 -dione as a yellow oil, $[\alpha]_D^{25} -21.42°$ (c, 0.994, CH$_2$Cl$_2$).

EXAMPLE 22

(R)-2-[3-(Acetyloxy)-3-methyl-4-pentynyl]-3,5,6-trimethyl-2,5-cyclohexadiene-1,4-dione By the same procedure as in Example 21, the title compound was prepared form (R)-(−)-2-[3-hydroxy-3-methyl-4-pentynyl]-3,5,6-trimethyl-2,5-cyclohexadiene-1,4-dione. The reaction produced (R)-2-[3-(acetyloxy)-3-methyl-4-pentynyl]-3,5,6-trimethyl-2,5-cyclohexadiene-1,4-dione as a yellow oil $[\alpha]_D^{25} +22.87°$, (c 1.08. CH$_2$Cl$_2$).

EXAMPLE 23

(S)-(+)-2-Ethynyl-3,4-dihydro-2,5,7,8-tetramethyl-2H-1-benzopyran-6-ol, from (R)-(−)-2-[3-hydroxy-3-methyl-4-pentynyl]-3,5,6-trimethyl-2,5-cyclohexadiene-1,4-dione, (cyclization with inversion)

(A) A mixture of 370 mg (1.5 mmol) of [[$\alpha]_D^{25} -11.9°$, (CH$_2$Cl$_2$)](R)-(−)-2-[3-hydroxy-3-methyl-4-pentynyl]-3,5,6-trimethyl-2,5-cyclohexadiene-1,4-dione, 0.31 mL of triethylamine, and 3.6 mg of 4-dimethylamino pyridine in 4 mL of dry CH$_2$Cl$_2$ was cooled in an ice-bath, and stirred under argon. A solution of methanesulfonyl chloride (0.15 mL) in 0.5 mL of CH$_2$Cl$_2$ was then added dropwise. The reaction was stirred at 0° C.–4° C. for 6 h, then taken into 60 mL of cold CH$_2$Cl$_2$. It was washed with 1.0N HCl, saturated NaHCO$_3$ solution, water, and dried over anhydrous MgSO$_4$. It was filtered and pyridine (3 drops) was added to the filtrate. Concentration of solvent at 0° C. in vacuo gave a yellow oil, which was dissolved in CH$_2$Cl$_2$ and evaporated twice at 0° C. The resultant crude mesylate of the (R)-(−)-quinone was used immediately for the reaction described below.

The crude mesylate (0.75 mmol) was dissolved in isopropyl alcohol (3 mL), THF (3 mL), cooled in an ice-bath, and degassed with argon. Sodium borohydride (60 mg) was added portionwise. The reaction mixture was stirred at 0°–4° C. for 1.5 h. (the yellow color of the quinone disappeared at 45 min). Triethylamine (200 mg) was added and the mixture was stirred at 0°–4° C. for 2.0 h more, and further at 25° C. for 0.5 h. The mixture was cooled again to 4° C. and treated carefully with cold water (1 mL), and aqueous acetic acid (1:3), then diluted with ether (100 mL). It was washed with diluted HCl, water, and dried over anhydrous MgSO$_4$. Concentration of solvent in vacuo gave 160 mg of solid. Flash chromatography (silica gel, with ether-petroleum ether 1:4) of this material yielded 40 mg of product, which on crystallization from 1:5 ether-hexane gave 21 mg of white solid, mp 90°–105° C., $[\alpha]_D^{25} +39.5°$, (CHCl$_3$). Recrystallization again twice afforded (S)-(+)-2-ethynyl-3,4-dihydro-2,5,7,8-tetramethyl-2H-1-benzopyran-6-ol as white needles: mp 110°–119° C., $[\alpha]_D^{25} +51.35°$, (CHCl$_3$).

B. A solution of 308 mg (1.07 mmol) of (R)-2-[3-(acetyloxy)-3-methyl-4-pentynyl]-3,5,6-trimethyl-2,5-cyclohexadiene-1,4-dione $[\alpha]_D^{25} +22.87°$, (CHCl$_3$) in 5 mL of CH$_3$OH was cooled to 0° C., and treated with NaBH$_4$ (64 mg, 1.69 mmol) in several portions. The reaction mixture was stirred at 0°–4° C. for 15 min., and then treated carefully with saturated NH$_4$Cl solution. It was then extracted with ether (3 times). The ethereal extracts were combined, washed with water, dried over MgSO$_4$, filtered, and concentrated at 38° C., in vacuo to give the nearly colorless hydroquinone, which was used immediately. Methylene chloride (6 mL) was added to this crude product, followed by 12 mg of AgClO$_4$.H$_2$O. The mixture was stirred at 22° C. for 17 h under argon, and further heated under reflux for 3.5 h. It was diluted with CH$_2$Cl$_2$ (50 mL), washed with dilute NH$_4$OH, 1.0 N HCl, water, and dried over anhydrous MgSO$_4$. Concentration of CH$_2$Cl$_2$ in vacuo gave 240 mg of brown residue. Flash column chromatography of this material on silica gel (14 g) using ether-petroleum ether (1:4) afforded 153 mg (62%) of crystalline product. Crystallization from ether-hexane (1:4) at −15° C. gave 49 mg of product =mp 105°–113° C., $[\alpha]_D^{25}+25.83°$, (c 1.01, CHCl$_3$). The mother liquor was concentrated and crystallized at 22° C. from ether-hexane (1:5) to yield 32 mg of (S)-(+)-2-ethynyl-3,4-dihydro-2,5,7,8-tetramethyl-2H-1-benzopyran-6-ol: mp 102°–113° C., $[\alpha]_D^{25}+53.31°$, (C 1.00, CHCl$_3$).

C. A solution of 285 mg (0.99 mmol) of (R)-2-[3-(acetyloxy)-3-methyl-4-pentynyl]-3,5,6-trimethyl-2,5-cyclohexadiene-1,4-dione in 4 mL of CH$_2$Cl$_2$ was stirred with 250 mg of Zn dust, and 250 mg of glacial acetic acid. The reaction mixture was stirred at 4° C. under argon for 50 min, then filtered. It was worked up with CH$_2$Cl$_2$ as described above. The crude hydroquinone acetate was taken into 6 mL of CH$_2$Cl$_2$ and treated with 20 mg of AgClO$_4$.H$_2$O as described above to give 124 mg of crude product after workup, and purification by flash chromatography. Crystallization of this material from toluene-hexane (1:1) at −15° C. gave 57 mg of (S)-2-ethynyl-3,4-dihydro-2,5,7,8-tetramethyl-2H-1-benzopyran-6-ol: $[\alpha]_D^{25}+20.20°$, (c1.3, CHCl$_3$).

EXAMPLE 24

Racemization of (R)-(−)-2-[3-hydroxy-3-methyl-4-pentynyl]-3,5,6-trimethyl-2,5-cyclohexadiene-1,4-dione A solution of 99 mg of (R)-(−)-2-[3-hydroxy-3-methyl-4-pentynyl]-3,5,6-trimethyl-2,5-cyclohexadiene-1,4-dione $[\alpha]_{D25}-11.99°$, (CH$_2$Cl$_2$), 10 mg of 4-N,N-dimethyl pyridine, 61 mg of triethylamine in 1.5 mL of CH$_2$Cl$_2$ was treated with methanesulfonyl chloride (40 µl) at 0° C., under argon. The reaction mixture was stirred at 0° C. for 2.5h. Workup as described in Example 23 to gave the corresponding crude mesylate as a yellow oil. It was dissolved in 2 mL of THF, cooled in an ice-bath, and treated with 6 mg of AgNO$_3$ in approximately 0.3 mL of water. The reaction mixture was stirred at 0° C. for 15 min., then at 25° C. for 2 h. saturated NH$_4$Cl solution (50 mL) was added, and it was extracted with CH$_2$Cl$_2$ (3×20 mL). Methylene chloride extracts were combined, washed with water, dried over MgSO$_4$, filtered, and concentrated in vacuo to give 100 mg of yellow oil. It was flash chromatographed on silica gel (7 g) and eluted with ether-petroleum ether (1:5) to give 51 mg of (S)-(+)-2-[3-hydroxy-3-methyl-4-pentynyl]-3,5,6-trimethyl-2,5-cyclohexadiene-1,4-dione as a yellow oil, $[\alpha]_D^{25}6.6°$ (CH$_2$Cl$_2$), shown by NMR to be 50% e.e.

EXAMPLE 25

Racemization of (R)-(−)-5-[2,5-Bis(acetyloxy)-3,4,6-trimethylphenyl]-3-methyl-1-pentyn-3-ol A solution of 166 (0.5 mmol) of (R)-(−)-5-[2,5-bis(acetyloxy)-3,4,6-trimethylphenyl]-3-methyl-1-pentyn-3-ol ($[\alpha]_D^{25}-15.4°$, CHCl$_3$), 76 mg of triethylamine, 12 mg (0.1 mmol) of 4-N,N-dimethylaminopyridine in 2 mL of CH$_2$Cl$_2$, was stirred at 0° C. under argon, and treated dropwise with 72 mg (0.63 mmol) of methanesulfonyl chloride in 0.5 mL of CH$_2$Cl$_2$. The reaction mixture was stirred at 0° C. for 2.5 h, diluted with CH$_2$Cl$_2$ (about 50 mL), washed twice with cold 1N HCl, cold saturated NaHCO$_3$ solution, and dried over MgSO$_4$. Concentration of CH$_2$Cl$_2$ at 4° C. (4 drops of pyridine was added to the solution) gave the crude mesylate as a colorless residue. This was taken into 2.4 mL of THF and cooled in an ice-bath. A solution of AgNO$_3$ (8 mg, 0.047 mmol) in 0.4 mL of H$_2$O was added, and the reaction mixture was stirred at 25° C. for 2 h under argon. Workup as described in Example 24 gave 168 mg of crude product which on crystallization from ether-petroleum ether afforded 83 mg of 5-[2,5-bis-(acetyloxy)-3,4,6-trimethylphenyl]-3-methyl-1-pentyn-3-ol as white crystals=mp 100°–106° C., $[\alpha]_D^{25}+1.7°$ (CHCl$_3$).

EXAMPLE 26

(S)-(+)-2-Ethynyl-3,4-dihydro-2,5,7,8-tetramethyl-2H-1-benzopyran-6-ol (A) From (S)-1,2-Benzenedicarboxylic acid[3-[2,5-bis(acetoxy3,4,6-trimethylphenyl]-1-ethynyl-1-methylpropyl]ester 48.0 g (0.1M) of S-(+)-1,2-benzenedicarboxylic acid [3-(2,5)-bis(acetyloxy)-3,4,6-trimethylphenyl]-1-ethynyl-1-methylpropyl]ester was dissolved in 250 mL of methyl alcohol and degassed with argon. To this solution, 150 mL (0.9M) of 6N NaOH was added dropwise. It was then refluxed for 1.0 h, cooled to ~4° C., and acidified to pH 1.5 with 150 mL of 5.6 N H$_2$SO$_4$. 200 mL of MeOH and 5 mg of (S)-(+)-2-[3-hydroxy-3-methyl-4-pentynyl]-3,5,6-trimethyl-2,5-cyclohexadiene-1,4-dione were added. The reaction mixture was heated under reflux for 18 h. Another 20 mg of (S)-(+)-2-[3-hydroxy-3-methyl-4-pentynyl]-3,5,6-trimethyl-2,5-cyclohexadiene-1,4-dione was added again and refluxing was continued for 26 h more for completion of the reaction. It was cooled to 25° C. and 500 mL of water was added. The mixture was extracted with 3×300 mL diethyl ether. The ether extracts were combined, washed successively with 3×300 mL saturated sodium bicarbonate solution, 3×300 mL 1 N HCl, 3×300 mL water, and dried over anhydrous MgSO$_4$ after filtration, the ether solution was further passed through a short plug of 500 g of forisil which was further washed with 500 mL ether. Evaporation of ether in vacuo gave 23 g of orange-tan solid. Crystallization of this material from toluene/hexane (1:5) gave 15.62 g of (S)-(+)-2-ethynyl-3,4-dihydro-2,5,7,8-tetramethyl-2H-1-benzopyran-6-ol as needles: mp +109°–114° C., $[\alpha]_D^{25}53.46°$ (C. 0.997, CHCl$_3$). A second crop of 2.94 g of this compound was also obtained, mp 108°–117° C., $[\alpha]_D^{25}+53.63°$ (C. 0.985, CHCl$_3$). A total yield (80.5%) 18.56 g of product was obtained.

(B) From (S)-(−)-Benzoic acid [3-[2,5-bis(acetoxy 3,4,6-trimethylphenyl]-1-ethynyl-1-methylpropyl]ester In the same manner as described in part A of this Example, 92 mg of (S)-(+)-2-ethynyl-3,4-dihydro-2,5,7,8-tetramethyl-2H-1-benzopyran-6-ol $[\alpha]_D^{25}+53.93°$ (CHCl$_3$) was prepared from 218 mg of (S)-(−)-benzoic acid [3-[2,5-bis(acetoxy3,4,6-trimethylphenyl]-1-ethynyl-1-methylpropyl]ester ($[\alpha]_D^{25}-17.05°$ CHCl$_3$).

(C) From (S)-(+)-2-[3-hydroxy-3-methyl-4-pentynyl]-3,5,6-trimethyl-2,5-cyclohexadiene-1,4-dione A mixture of 500 mg (2.0 mmol) of (S)-(+)-2-[3-hydroxy-3-methyl-4-pentynyl]-3,5,6-trimethyl-2,5-cyclohexadiene-1,4-dione ($[\alpha]_D^{25}+11.39°$, CH$_2$Cl$_2$) and 500 mg of Zinc dust in 0.25 mL of glacial acetic acid and 5 mL of CH$_2$Cl$_2$ was stirred at 25° C. for 15 minutes. The mixture was filtered over 5 g of Celite and washed with CH$_2$Cl$_2$. After removal of CH$_2$Cl$_2$ in vacuo the white residue was dissolved in 10 mL of methanol containing 1 mL of 5.6 N H$_2$SO$_4$, and 1 mg of the S-(+)-quinone i.e. (S)-(+)-2-[3-hydroxy-3-methyl-4-pentynyl]-3,5,6-trimethyl-2,5-cyclohexadiene-1,4-dione. The solution was refluxed for 5 h, cooled to 25° C., and taken into water. This was extracted with ether (2×100 mL). The ether extracts were combined, washed with water (2×100 mL) and dried over anhydrous MgSO$_4$. Filtration and concentration of solvent in vacuo gave 466 mg of tan solid [α]$_D^{25}$+52.05°, (CHCl$_3$). Recrystallization from ether/hexane (1:5) yielded 320 mg (65%) of (S)-(+)-2-ethynyl-3,4-dihydro-2,5,7,8-tetramethyl-2H-1-benzopyran-6-ol as white needles (65% yield): [α]$_D^{25}$+55.66° (CHCl$_3$).

EXAMPLE 27

(S)-(+)-2-Ethynyl-3,4-dihydro-2,5,7,8-tetramethyl-6-(phenylmethoxy)-2H-1-benzopyran (A) From
(S)-(+)-2-ethynyl-3,4-dihydro-2,5,7,8-tetramethyl-1-2H-benzopyran-6-ol A mixture of (S)-(+)2-ethynyl-3,4-dihydro-2,5,7,8-tetramethyl-2H-benzopyran-6-ol (220 mg, 0.87 mmol), powdered anhydrous potassium carbonate (360 mg, 2.6 mmol), and benzyl chloride (330 mg, 2.6 mmol) in 1.5 mL of dimethylformamide was stirred vigorously at 25° C. under argon for 20 h. This reaction mixture was taken into water and extracted with diethyl ether (3×40 mL). The combined ether extracts were washed with water, dried over MgSO$_4$ and concentrated in vacuo to give an oily solid.

Purification of this material by column chromatograph on silica gel (10 g. eluent=ether/petroleum ether (30°-60° 2:3 parts by volume) afforded 260 mg of white solid. Crystallization from ether/petroleum ether (1:2 parts by volume) at 4° gave 96 mg of (S)-(+)-2-ethynyl-3,4-dihydro-2,5,7,8-tetramethyl-6-(phenylmethoxy)-2H-1-benzopyran as white needles: mp 85°-92° C., [α]$_D^{25}$+48.33°, (C. 0.915, CHCl$_3$).

(B) From
S-(+)-6-Benzyloxy-2-formyl-2,5,7,8-tetramethyl Chroman

A solution of 766 mg (3.0 mmol) of diethyl trichloromethane phosphono acetate in a mixture of ether (30 mL) and dry tetrahydrofuran (THF) (15 mL) was cooled to −98° C. (liquid nitrogen-methanol bath). Butyl lithium (3.0 mmol, 1.76 mL, 1.7N in hexane) was added dropwise and the mixture was stirred at −98° C., under argon for 10 minutes. A solution of the (S)-(+)-6-benzyloxy-2-formyl-2,5,7,8-tetramethyl chroman, (648 mg, 2.0 mmol) in 10 mL of dry ether was added, it was allowed to equilbrate to 25° C. over a period of 1.0 h. Then the reaction mixture was heated (70° C., bath temperature) under reflux for 2.0 h. This mixture was cooled again to −70° C. and treated carefully with 6 mL of 6N H$_2$SO$_4$. It was then warmed to 25° C., diluted with water (100 mL, and extracted with ether (3×100 mL). The combined ether extracts were washed with saturated sodium bisulfite (3×100 mL), dried over anhydrous MgSO$_4$, filtered, and concentrated in vacuo to give an oil. This was quickly passed through a column of silica gel (30 g). Elution with 5% ether in petroleum ether (30°-60° C.) gave 751 mg of oily substance.

This above product as a colorless oil was taken into 2 mL of dry THF and 2 mL of dry ether, cooled to −70° C. A solution of n-butyl lithium (2.0 mL, 1.7N in hexane) was added dropwise and the reaction mixture was stirred at −70° under argon for 0.5 h. Dilute sulfuric acid (2.0N, 6 mL) was added and the mixture was allowed to reach 25° C. over a period of 1.0 h. It was diluted with water and workup with ether in the usual manner to give 385 mg of solid, crystallization of which from ether/petroleum ether (1:12) afforded 149 mg (23% yield) of (S)-(+)-2-ethynyl-3,4-dihydro-2,5,7,8-tetramethyl-6-(phenylmethoxy)-2H-1-benzopyran as white needles: mp 88°-90° C., [α]$_D^{25}$+45.71°, (1.12, CHCl$_3$).

EXAMPLE 28

(S)-(+)-2-Ethynyl-3,4-dihydro-6-methoxy 2,5,7,8-tetramethyl-2H-1-benzopyran

A solution of (S)-(+)-2-ethynyl-3,4-dihydro-2,5,7,8-tetramethyl-2H-1-benzopyran-6-ol (354 mg, 1.54 mmol) in acetone (9 mL) was treated with dimethyl sulfate (0.8 mL), and 50% NaOH (1.2 mL) for 2 h at 25° C. with stirring. Ammonium hydroxide solution (1.0N, 50 mL) was added, and it was extracted with ehter (3×50 mL). The extracts were combined, washed with 1.0N HCl, water, and dried over MgSO$_4$. It was filtered and concentrated in vacuo to give 400 mg of solid, which or crystallization from ether-hexane (1:12) afforded 141 mg (47%) of (S)-(+)-2-ethynyl-3,4-dihydro-6-methoxy-2,5,7,8-tetramethyl-2H-1-benzopyran as white prisms: mp 94°-97° C., [α]$_D^{25}$+53.86°, (c 0.4233, CHCl$_3$).

EXAMPLE 29

(S)-(+)-2-Ethynyl-3,4-dihydro-2,5,7,8-tetramethyl-2H-1-benzopyran-6-ol acetate

A mixture of 150 mg (0.65 mmol) of (S)-(+)-2-ethynyl-3,4-dihydro-2,5,7,8-tetramethyl-2H-1-benzopyran-6-ol, 0.5 mL of pyridine and 0.5 mL of acetic anhydride was stirred at 25° C. for 16 h. It was taken into 100 mL of ether, and washed successfully with 1.0N HCl, saturated NaHCO$_3$ solution, water, and dried over MgSO$_4$. Removal of ether in vacuo yielded 180 mg of colorless oil which on crystallization from ether-hexane (1:9) afforded 59 mg of (S)-(+)-2-ethynyl-3,4-dihydro-2,5,7,8-tetramethyl-H-1-benzopyran-6-ol acetate as a white solid: mp 82°-84° C., [α]$_D^{25}$+58.37°, (c 0.956, CHCl$_3$).

EXAMPLE 30

(R)-(−)-2-Ethynyl-3,4-dihydro-2,5,7,8-tetramethyl-2H-1-benzopyran-6-ol

Based on the procedure described in Example 26, part A, 18.1 g of (R)-(−)-2-ethynyl-3,4-dihydro-2,5,7,8-tetramethyl-2H-1-benzopyran-6-ol was prepared in a 78% yield from 48 g of (R)-1,2-benzenedicarboxylic acid [3-[2,5-bis(acetyloxy)-3,4,6-trimethylphenyl]-1-ethynyl-1-methylpropyl]ester. The product was produced as white needles: mp 109°-114° C., [α]$_D^{25}$−55.72°, (c 1.001, CHCl$_3$).

EXAMPLE 31

(R)-(−)-2-Ethynyl-3,4-dihydro-2,5,7,8-tetramethyl 6-(phenylmethoxy)-2H-1-benzopyran By the same procedure as described in Example 27, part A, 199 mg of (R)-(−)-2-ethynyl-3,4-dihydro-2,5,7,8-tetramethyl 6-(phenylmethoxy)-2H-1-benzopyran was obtained from 419 mg of (R)-(−)-2-ethynyl-3,4-dihydro-2,5,7,8-tetramethyl-H-1-benzopyran-6-ol. This product was produced as a white solid=mp 93°-95° C.

(from 1:6 ether-petroleum ether). [α]$_D^{25}$−46.88°, (c 0.92, CHCl$_3$).

EXAMPLE 32

(S)-(+)-2-[3-Hydroxy-3-methyl-4-pentynyl]-3,5,6-trimethyl-2,5-cyclohexadiene-1,4-dione A solution of ferric chloride hexahydrate (486 mg) in 6 mL of 1:1 H$_2$O/CH$_3$OH was added portionwise at 25° C. over a period of 3.0 h, (1.0 mL/0.5 h), to stirred solution of 150 mg of (S)-(+)-3,4-dihydro-2-ethynyl-2,5,7,8-tetramethyl-2H-1-benzopyran-6-ol([α]$_D^{25}$+56.14°, CHCl$_3$). The reaction mixture was further stirred at 25° C. for 0.5 h, and diluted with water (100 mL). It was extracted with ether (3×100 mL). Ether extracts were combined, washed with water, dried over MgSO$_4$, filtered and concentrated in vacuo to give 181 mg of yellow oil. This was flash chromatographed on silica gel (25 g, 230–400 mesh) using 1:1 ether-petroleum ether (30°–60° C.) as eluent to give 164 mg of (S)-(+)-2-[3-hydroxy-3-methyl-4-pentynyl]-3,5,6-trimethyl-2,5-cyclohexadiene-1,4-dione as a yellow oil. Crystallization of the yellow oil from ether-petroleum ether (1:12) afforded 87 mg of (S)-(+)-2-[3-hydroxy-3-methyl-4-pentynyl]-3,5,6-trimethyl-2,5-cyclohexadiene-1,4-dione as yellow needles: mp 80°–82° C., [α]$_D^{25}$+15.81°, (CHCl$_3$).

EXAMPLE 33

(R)-(−)-2-[3-Hydroxy-3-methyl-4-pentynyl]-3,5,6-trimethyl-2,5-cyclohexadiene-1,4-dione By the same procedure as described in Example 34, 160 mg of the (R)-(−)-quinone i.e. (R)-(−)-2-[3-hydroxy-3-methyl-4-pentynyl]-3,5,6-trimethyl-2,5-cyclohexadiene-1,4-dione was prepared from 150 of R-(+)-3,4-dihydro-2-ethynyl-2,5,7,8-tetramethyl-2H-1-benzopyran-6-ol [[α]$_D^{25}$−54.72°, CHCl$_3$] optically pure by NMR analysis.

EXAMPLE 34

(R)-(−)-2-Ethynyl-3,4-dihydro-6-methoxy-2,5,7,8-tetramethyl-2H-1-benzopyran

By the same procedure as described in Example 28 (R)-2-ethynyl-3,4-dihydro-6-methoxy-,5,7,8-tetramethyl-H-1-benzopyran was prepared from (R)-(−)2-ethynyl-3,4-dihydro-2,5,7,8-tetramethyl-2H-1-benzopyran-6-ol. This product was produced as white prisms=9-3°–95° C. [α]$_D^{25}$−57.14°, (C 0.28, CHCl$_3$).

EXAMPLE 35

(R)-2-Ethynyl-3,4-dihydro-2,5,7,8-tetramethyl-2H-1-benzopyran-6-ol acetate

Similar to the procedure described in Example 29 (R)-2-ethynyl-3,4-dihydro-2,5,7,8-tetramethyl-H-1-benzopyran-6-ol acetate was obtained from (R)-2-ethynyl-3,4-dihydro-2,5,7,8-tetramethyl-2H-1-benzopyran-6-ol. The acetate was obtained as a white solid=mp 81°–83° C., [α]$_D^{25}$−58.45°, (C 0.90, CHCl$_3$).

EXAMPLE 36

[2S-(4R*,8R*,)]-3,4-Dihydro-2,5,7,8-tetramethyl-2-(4,8,12-trimethyl-1-tridecynyl)-6-(phenylmethoxy)-2H-1-benzopyran A solution of 1.8 g (5.6 mmol) of (S)-(+)-3,4-dihydro-2-ethynyl-2,5,7,8-tetramethyl-2-(phenylmethoxy)-1-2H-benzopyran in 15 mL of dry THF was cooled to −75° C. under argon, and treated dropwise with 3.4 mL (5.8 mmol) of n-butyl lithium (1.7N in hexane). The mixture was stirred at −75° C. for 15 min. and then at 35° C. for 1 h under argon. It was cooled to 0° C., and a solution of (2R,6R)-(−)-1-bromo-2,6,10-trimethyl undecane (1.7 g, 6.1 mmol) in 15 mL of dry hexamethylphosphor amide was added. The reaction mixture was stirred under argon at 0° C. for 2 h, then at 25° C. for 2 h, and finally at 10° C. for 18 h. Saturated ammonium chloride (50 mL) was added and the crude product was isolated with ether in the usual manner and purified by HPLC to give 1.01 g of [2S-(4R*,8R*)]-3,4-dihydro-2,5,7,8-tetramethyl-2-(4,8,12-trimethyl-1-tridecynyl)-6-(phenylmethoxy)-2H-1-benzopyran, as a pale yellow oil: [α]$_D^{25}$+25.92°, (CHCl$_3$).

EXAMPLE 37

(2R,4′R,8′R)-α-Tocopherol

A mixture of [2S-(4R*,8R*,)]-3,4-dihydro-2,5,7,8-tetramethyl-2-(4,8,12-trimethyl-1-tridecynyl)-6-(phenylmethoxy)-2H-1-benzopyran, (200 mg, 0.39 mmol) and 40 mg of Raney Nickel in 5 mL of ethanol and 5 mL of ethyl acetate was hydrogenated at 25° C. and atmospheric pressure for 6 h. Workup in the usual manner and purification of the crude product by chromatography on silica gel (eluent 1:5 ether-hexanes) gave 170 mg of (2R,4′R,8′R)-α-tocopherol as a pale yellow oil, identical in all aspects with a known sample.

We claim:

1. A process of resolving a racemate of the formula:

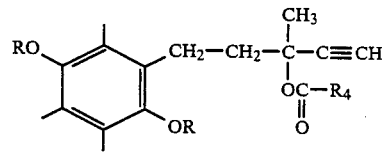

wherein
R taken together with its attached oxygen atom forms a hydrolyzable ester protecting group and
R$_4$ is phenyl or phenyl substituted which from 1 to 3 halo groups;
into its two optical antipodes one of which has the formula:

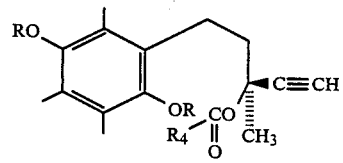

wherein R and R$_4$ are as above:
and the other of which has the formula

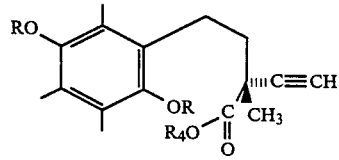

wherein R and R$_4$ are as above;
comprising forming a solution by dissolving said racemate in an inert hydrocarbon solvent and crystallizing one of said antipodes from said solution while leaving the other of said antipodes in solution.

2. The process of claim 1 wherein said solution is formed and said crystallization occurs at a temperature of from −25° C. to 30° C.

3. The process of claim 1 wherein said solvent is an aromatic hydrocarbon solvent.

4. The process of claim 3 wherein said crystallization is carried out by seeding said solution with at least one crystal of the optical antipode which is to be crystallized from said solution.

5. The process of claim 4 wherein said solvent is toluene.

6. An optically active antipode of the formula:

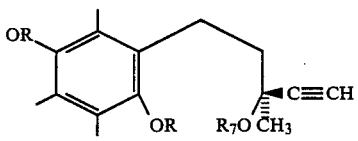

wherein
R taken together with its attached oxygen atom forms a hydrolyzable ester protecting group; $R_7$ is hydrogen,

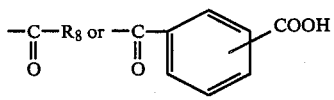

and
$R_8$ is phenyl or phenyl substituted with from 1 to 3 halo groups.
said antipode being substantially free of its other optically active antipodes.

7. The antipode of claim 6 wherein $R_7$ is hydrogen.
8. The antipode of claim 7 wherein R is acetyl.
9. The antipode of claim 6 wherein $R_7$ is

10. The antipode of claim 9 wherein $R_8$ is phenyl.
11. The antipode of claim 9 wherein R is acetyl.
12. An optically active antipode of the formula:

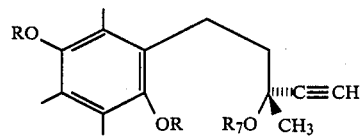

wherein
R taken together with its attached oxygen atom forms a hydrolyzable ester protecting group;
$R_7$ is hydrogen,

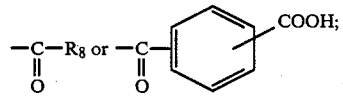

and
$R_8$ is phenyl or phenyl substituted with from 1 to 3 halo groups
said antipode being substantially free of its other optically active antipode.

13. The antipode of claim 12 wherein $R_7$ is hydrogen.
14. The antipode of claim 13 wherein R is acetyl.
15. The antipode of claim 12 wherein $R_7$ is

16. The antipode of claim 15 wherein $R_8$ is phenyl.
17. The antipode of claim 16 wherein R is acetyl.

* * * * *